United States Patent
Wu

(10) Patent No.: US 8,292,890 B2
(45) Date of Patent: Oct. 23, 2012

(54) BONE DILATOR

(76) Inventor: Naiqing Wu, Nanjing (CN)

( * ) Notice: Subject to any disclaimer, the term of this patent is extended or adjusted under 35 U.S.C. 154(b) by 734 days.

(21) Appl. No.: 12/050,860

(22) Filed: Mar. 18, 2008

(65) Prior Publication Data
US 2008/0177259 A1    Jul. 24, 2008

Related U.S. Application Data

(63) Continuation-in-part of application No. PCT/CN2006/002441, filed on Sep. 19, 2006.

(30) Foreign Application Priority Data

Sep. 19, 2005    (CN) .......................... 2005 1 0094420

(51) Int. Cl.
    *A61B 17/00*    (2006.01)
(52) U.S. Cl. ................. 606/57; 606/63; 606/90
(58) Field of Classification Search ............ 606/60, 606/79, 139, 170, 191, 198, 204, 90, 99; 600/80, 203, 204, 214, 225, 591
    See application file for complete search history.

(56) References Cited

U.S. PATENT DOCUMENTS

| | | | | |
|---|---|---|---|---|
| 832,201 | A * | 10/1906 | Kistler | 604/108 |
| 3,667,474 | A * | 6/1972 | Lapkin et al. | 606/198 |
| 4,204,548 | A * | 5/1980 | Kurz | 600/591 |
| 5,113,846 | A * | 5/1992 | Hiltebrandt et al. | 600/225 |
| 5,235,966 | A * | 8/1993 | Jamner | 600/204 |
| 5,307,805 | A * | 5/1994 | Byrne | 600/214 |
| 5,827,289 | A | 10/1998 | Reiley et al. | |
| 6,383,188 | B2 * | 5/2002 | Kuslich et al. | 606/80 |
| 2004/0087994 | A1 | 5/2004 | Suddaby | |
| 2007/0239162 | A1 * | 10/2007 | Bhatnagar et al. | 606/69 |

FOREIGN PATENT DOCUMENTS

| CN | 2453957 | 10/2001 |
|---|---|---|
| CN | 1371752 | 10/2002 |

OTHER PUBLICATIONS

Internationl Search Report, Dec. 28, 2006.

* cited by examiner

*Primary Examiner* — Thomas Barrett
*Assistant Examiner* — Melissa A Golob
(74) *Attorney, Agent, or Firm* — Schwabe, Williamson & Wyatt, P.C.

(57) ABSTRACT

The present invention relates to a bone dilator designed for treating compression fracture of vertebral body, and fractures of cancellous bones at other sites. The bone dilator comprises a head portion, a neck portion, a connecting tube, a handle and a rotary hilt. The head portion embodies different shapes for use at different locations. When the rotary hilt is rotated clockwise and the pull rod is pulled backwards, the upper and the lower parts of the head portion keep parallel or at a predetermined angle during expanding. When the rotary hilt is rotated counterclockwise and the pull rod is pushed forwards, the head portion and the neck portion completely join together, the distal end of the pull rod and the bar stays are completely or partially retracted in grooves inside the head portion and the neck portion.

10 Claims, 4 Drawing Sheets

BONE DILATOR

RELATED APPLICATIONS

This is a continuation-in-part application of PCT Application No. PCT/CN2006/002441 filed on Sep. 19, 2006 which claims priority to Chinese Patent Application 200510094420.1 filed Sep. 19, 2005. Accordingly, this continuation-in-part application claims priority to PCT Application No. PCT/CN2006/002441 (Sep. 19, 2006) and to Chinese Patent Application 200510094420.1 (Sep. 19, 2005) (by way of PCT Application No. PCT/CN2006/002441). The disclosures of both PCT/CN2006/002441 and Chinese Patent Application 200510094420.1 are hereby incorporated by reference.

FIELD OF THE INVENTION

The present invention is related to a medical instrument for minimally invasive orthopedic operation, more particularly to a bone dilator, which is used mainly for treating osteoporotic compression fracture of vertebral body. This instrument can also be used for treating fractures of cancellous bones at other sites and certain traumatic or pathologic compression fracture of vertebral body.

BACKGROUND OF THE RELATED ART

Osteoporosis is a common disease menacing the health of senior people. There are 88,900,000 patients suffering from osteoporosis, which ranks the sixth in all diseases in China in the year 2002. Compression fracture of vertebral body caused by osteoporosis is one of the serious complications. There are 44,000,000 people afflicted with osteoporosis in the United States in 2002. Every year 700,000 out of 1,500,000 fracture cases as a result thereof are spine fractures and half of the patients need hospitalization and surgical treatments. Severe spine fractures may lead to injury of the spinal cord and even paraplegia. The vital capacity decreases by nine percent in the case of compression fracture of one thoracic vertebral body. Mortality of vertebral compression fracture is 23% to 34% within five years. Currently, there are principally two minimally invasive surgical methods for the treatment of the osteoporotic compression fracture of vertebral body:

1. Deramond in France first introduced the percutaneous injection of bone cement into the vertebral body in 1984. The technique is called percutaneous vertebroplasty, and abbreviated as PV. The application of PV for the osteoporotic compression fracture of vertebral body can enhance the strength and stability of the vertebral body, as well as relieve pain. Whereas it can neither increase the height of the compressed vertebral body, nor can it rectify kyphosis. It also has a high leakage rate of the bone cement.
2. Reiley, et al., in the United States designed a technique to rectify kyphosis by means of a new inflation balloon on the basis of inflation balloon of blood vessels in 1994. The technique is called balloon-kyphoplasty and abbreviated as BK. The balloon is inserted into the vertebral body via or from outside of the vertebral pedicle and inflated to restore the height of the compressed vertebral body. A cavity is created inside the vertebral body after the balloon is removed. Then the bone cement is injected into the cavity in the vertebral body. This technique was granted to a U.S. patent under U.S. Pat. No. 5,827,289 in 1998, and was ratified for clinical practice by FDA in 1998. The design purposes of BK are: 1) to restore the height of the compressed vertebral body and rectify kyphosis; and 2) to achieve lower pressure during the injection of bone cement so as to reduce leakage of bone cement. However, a clinical research of BK treatment on 70 vertebral bodies of 30 patients showed that the lost heights were restored by 33.1% and an average restoration was 2.9 mm. The seventy treated vertebral bodies were divided into two groups. One group without height restoration accounts for 30%, and the other group with height restoration accounts for 70%. The average height of the vertebral bodies increases by 4.1 mm, namely by 46.8% in the latter group. Moreover, leakage rate of bone cement is 8.6% in both groups which is similar to that in the treatment of osteoporotic compression fracture of vertebral body by PV. Many other literatures also reported the similar restoration rate of the heights of vertebral bodies and leakage rate of the bone cement. Accordingly, BK has apparently defects in the following aspects:

(1) Clinical practice of BK can only restore on average ⅓ of the lost heights of vertebral bodies. The result is far from the claimed in the design. Patients treated with BK are still obviously kyphotic. As a matter of fact, such a clinical treatment result is predetermined based on the structure of the balloon. According to the principle of hydrodynamics, a pressurized balloon will inflate along the direction of least resistance. Thus, the balloon inflates significantly at the site of fracture, especially at the site of comminuted fracture. Whereas at upper and lower end plates, where restoration to the height of the vertebral body is mostly needed, the inflation is suppressed due to greater resistance.

(2) Leakage rate of the injected bone cement is still relatively high due to the limited restoration in the height of the vertebral body.

(3) Although BK pertains to minimally invasive surgery, the cost of one balloon is very high. This constitutes an enormous economic burden to senior patients suffering from osteoporotic compression fracture of vertebral body. Moreover, since the balloon is easy to be pierced by the sharp bone chips during placement or inflation, the replacement of the balloon is needed, thus aggravating the economic burden on the patients.

Therefore a pressing task in the treatment of osteoporotic compression fracture of vertebral body is to develop a low-cost minimally invasive surgical instrument that not only can substantially restore the lost height of the compressed vertebral body and rectify kyphosis, but also can reduce the leakage rate of the bone cement.

SUMMARY OF THE INVENTION

In view of the deficiencies in the two minimally invasive surgical methods, namely PV and BK, broadly used in the treatment of osteoporotic compression fracture of vertebral body, the objective of the present invention is to provide a bone dilator to perform kyphoplasty by means of percutaneous bone dilation, which is suitable for minimally invasive surgery in senior patients. It can restore lost height of the vertebral body, rectify kyphosis, reduce bone cement leakage, and cut cost. It is also applicable for treating fractures of cancellous bones at other sites and certain traumatic or pathologic compression fracture of vertebral body.

For this purpose, the bone dilator according to this invention is implemented by the following solution: a bone dilator, comprises a head portion, a neck portion, a connecting tube, a handle and a rotary hilt; the head portion and the neck portion are integrated as a whole via hinged joint therebetween; the head portion, the neck portion, the connecting tube and the handle are hollow bodies, through which a pull rod penetrates; the rotary hilt is connected to a tension bolt, which is connected to one end of the pull rod; another end of the pull rod is provided with bar stays at both sides thereof, and the two ends of the bar stays are movably connected to the pull rod and the head portion via pins; a distal end of the connecting tube is movably connected to a proximal end of the neck portion, and a proximal end of the connecting tube is fixedly connected to a distal end of the handle; a distal end of a hilt support is disposed at a proximal end side of the handle, and the rotary hilt is movably connected to a proximal end side of the hilt support.

In comparison with the state of the art, the bone dilator according to this invention has the following advantages and characteristics:

1. The bone dilator according to this invention has a reasonable design and a compact structure. It enters the vertebral body posteriorly and percutaneously via or outside of the vertebral pedicle with perfect convenience, and makes the upper and lower end plates of the compressed vertebral body parallel or approximately parallel to each other when dilated. The bone dilator can substantially or completely restore the lost height of the vertebral body, whereas the balloon in the BK technique can only restore ⅓ of the lost height of the vertebral body, so that application of the bone dilator according to this invention can essentially rectify kyphosis. On measurement, the expansionary force of the bone dilator reaches more than 400 pounds per square inch, which is higher than the maximal pressure of 300 pounds per square inch achievable by the balloon inflation in BK. Moreover, the expansionary force is uniformly distributed, making it possible to expand along the direction with most resistance; this is in stark contrast to the balloon which inflates along the direction with least resistance. 18 vertebral bodies of 12 cases of osteoporotic compression fracture of vertebral body are treated by percutaneous dilator kyphoplasty, and the lost height of the vertebral body is averagely restored by 8.5 mm, namely 91%, thereby basically rectifying kyphosis. In each case the pain is notably alleviated.

2. Since the injection tube of the bone cement of the bone dilator according to this invention has an outer diameter of 4.5 mm and an inner diameter of 3.9 mm, which is obviously larger than an outer diameter of 3.4 mm and an inner diameter of 2.8 mm in the injection tubes of the bone cement of PV and BK, the timing for injecting the bone cement can be significantly postponed, so that the bone cement is injected during its dough state, rather than in the cases of PV and BK where injecting the bone cement must be carried out in advance during the drawing state of the bone cement. It is thus possible to markedly reduce leakage of the bone cement out of the vertebral body. Practical applications show that no leakage of the bone cement occurs in 18 vertebral bodies.

3. The bone dilator according to this invention is low in production cost, and can be applied for treating fractures of cancellous bones at other sites, and certain traumatic or pathologic compression fracture of vertebral body, etc.

DRAWINGS ACCOMPANYING THE DESCRIPTION (TAKING EXAMPLE Of A RACKET-SHAPED HEAD PORTION)

SPECIFIC EMBODIMENTS

Figure 1:
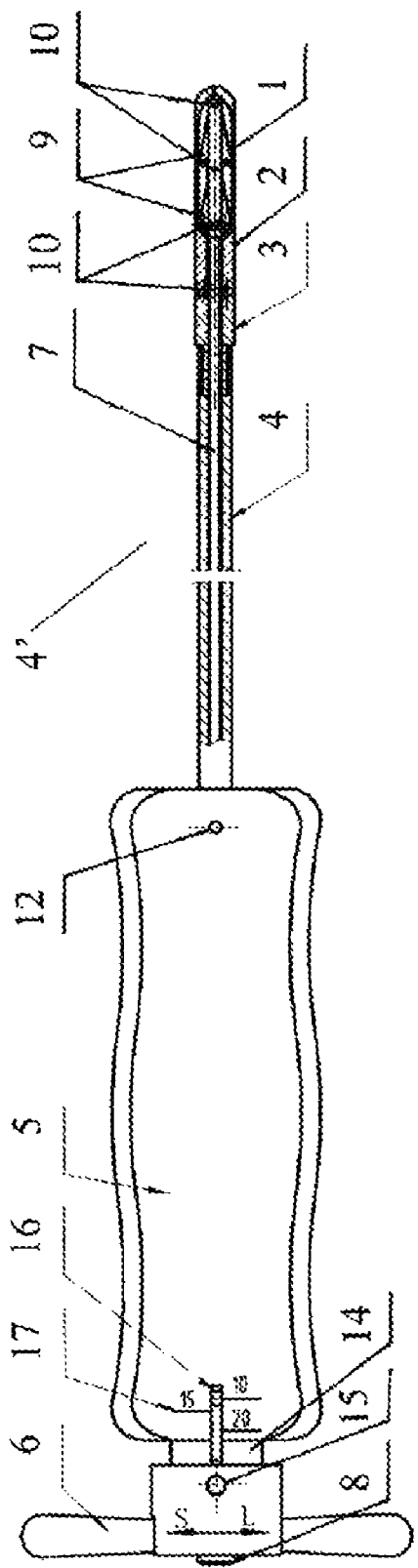
FIG. 1 is a front view showing the structure of the bone dilator according to the present invention.
Figure 2:
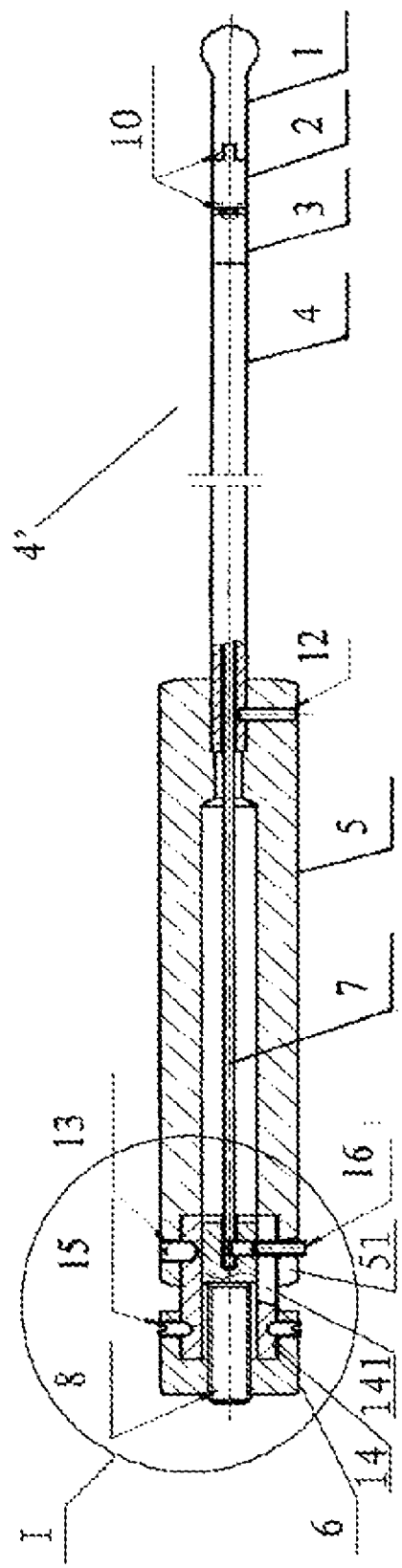
FIG. 2 is a plan view showing the structure of the bone dilator according to the present invention.

For illustration purpose, the right sides in FIGS. 1 and 2 are referred to as distal ends or fronts, and the left sides are referred to as proximal ends or rears.

In FIGS. 1-4, specific embodiments of the bone dilator according to the present invention are described in greater detail. The structure of the bone dilator according to the present invention comprises a head portion 1, a neck portion 2, a connecting tube 4', a handle 5, and a rotary hilt 6. The head portion 1, the neck portion 2, the connecting tube 4' and the handle 5 are all arranged as hollow bodies, through which a pull rod 7 penetrates. The head portion 1 and the neck portion 2 are integrated as a whole via hinged joint therebetween. At the center of the rotary hilt 6 is disposed a tension bolt 8, which is connected to a proximal end of the pull rod 7.

To make it easier for fabrication, the connecting tube 4' can also consist of a connecting tube body 4 and a waist portion 3, and such a combination has the same function, working principle and movement process as in the case of the connecting tube 4' alone. Specific configuration and working principle of the present invention are described in detail in the following paragraphs with such a structure as an example.

The head portion 1 consists of two parts of the same or dissimilar shapes, which can be embodied in different shapes for use at different locations, for instance, racket-shaped, rectangular shape, elliptical shape, circular shape or semicircular shape, etc., that is to say, the shape of the head portion 1 should match the shape of the location where it is to be used. The neck portion 2 assumes a shape of two semicircular tubes. The waist portion 3 is of a tubular shape.

Figure 4:
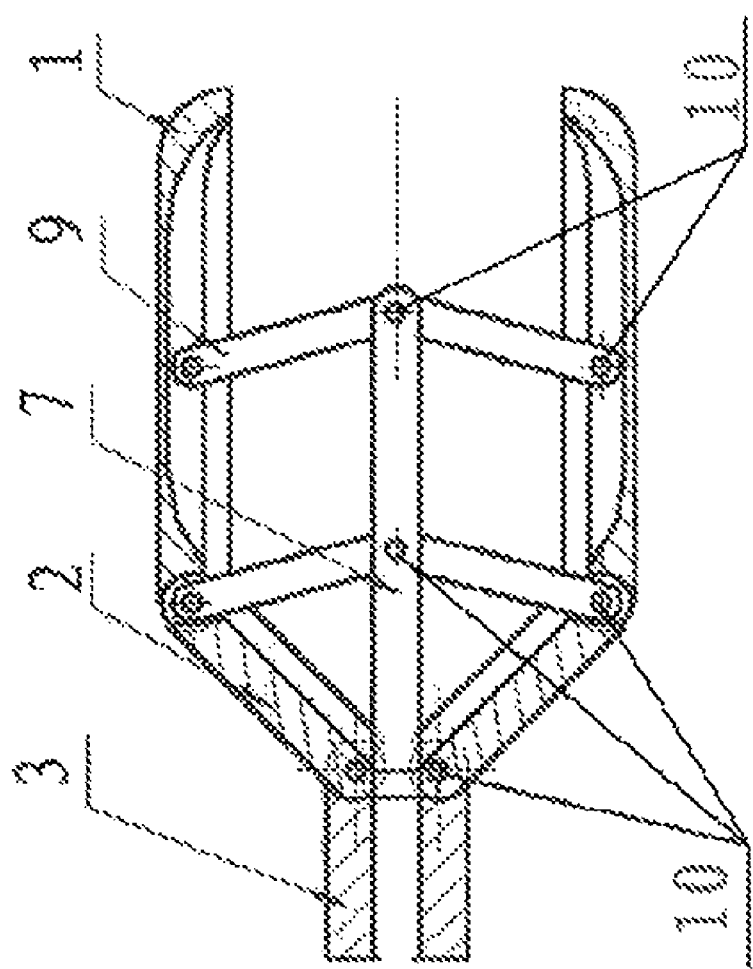
FIG. 4 is a sectional view showing the bone dilator according to the present invention, with the front in dilation.

The head portion 1 and the neck portion 2, as well as the neck portion 2 and the waist portion 3 are respectively connected to each other via hinges, namely via connecting pins 10 as shown in FIGS. 2 and 4. The distal end of the pull rod 7 is provided with at least two pairs of bar stays 9 at both sides thereof. As shown in FIG. 4, in this embodiment the distal end of the pull rod 7 is provided with two pairs of bar stays 9 at both sides thereof. The first ends of these two pairs of bar stays 9 are respectively movably connected to the pull rod 7 via the connecting pins 10, and the second ends thereof are movably connected to the inside of the head portion 1 via the connecting pins 10. In order to reduce the number of connecting members, as a feasible embodiment shown in FIG. 4, the connecting pins 10 extend through the second ends of the pair of bar stays 9 at the proximal end side, the distal end of the neck portion 2, and the proximal end of the head portion 1 to movably connect the three together. Grooves are provided inside the head portion 1 and the neck portion 2, such that, when the head portion 1 and the neck portion 2 are completely joined together, the distal end of the pull rod 7 and the bar stays 9 are completely or partially retracted in the grooves inside the head portion 1 and the neck portion 2. The connecting tube body 4 is a hollow and thin circular tube, whose outer diameter is equal to the outer diameters of the waist portion 3 and the completely joined neck portion 2, or less than the outer diameters of the waist portion 3 and the completely joined neck portion 2. The distal end of the connecting tube body 4 is connected to the proximal end of the waist portion 3 via screw threads, and the proximal end thereof is secured to the distal end of the handle 5 via a pin 12.

The distal end of a hilt support 14 is received in the proximal end side of the handle 5, and secured to the proximal end side of the handle 5 via a fastening screw 13. In this embodiment, the proximal end side of the handle 5 is provided with a stepped receiving groove, in which the distal end side of the hilt support 14 is received. An annular groove 142 is disposed on the peripheral surface of the proximal end side of the hilt support 14, and the distal end of the rotary hilt 6 is provided with a concave retracted groove 61, through which the distal end of the rotary hilt 6 is locked to the proximal end side of the hilt support 14. On the sidewall of the rotary hilt 6 is disposed at least one fixing member 15, whose front portion is retracted in the annular groove 142 on the peripheral surface of the hilt support 14, so that the rotary hilt 6 can rotate only at its original location and cannot move towards the direction of the proximal end or the distal end. The rotary hilt 6 is connected to the tension bolt 8 via screw threads. When the rotary hilt 6 rotates clockwise or counterclockwise, the tension bolt 8 moves towards the proximal end side or the distal end side in the axial direction, and thus generates a pulling force or pushing force on the pull rod 7.

Figure 3:
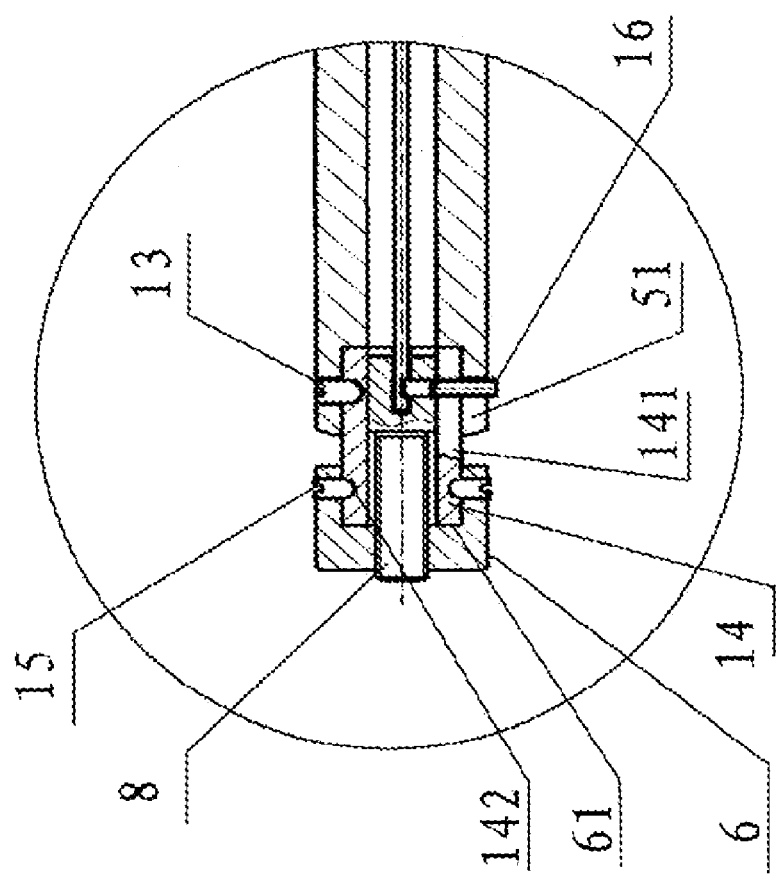
FIG. 3 is an enlarged partial view showing the portion in FIG. 2.

Corresponding longitudinally-opened grooves 51, 141 are disposed respectively at the proximal end side of the handle 5 and the distal end side of the hilt support 14. A pointer 16 passes through the longitudinally-opened grooves 51, 141 of the handle 5 as well as the hilt support 14 and is fixed with the tension bolt 8 or the pull rod 7. In this embodiment as shown in FIGS. 2 and 3, the pointer 16 is fixed with the tension bolt 8. When the rotary hilt 6 rotates clockwise or counterclockwise, the pointer 16 may move towards the proximal end side or the distal end side. The pointer 16 projects out of the longitudinally-opened grooves 51, 141, and a gauge 17 is provided at the edge of the opened grooves (referring to FIG. 1), so that the distance between the upper and lower parts of the head portion 1 upon dilation or joining can be read in millimeter using the pointer 16.

The working principle of the bone dilator according to the present invention is explained below.

The bone dilator consists of a front portion that generates an expansion force and a rear portion that generates a pulling or pushing force.

1. The front portion of the bone dilator comprises the head portion 1, the neck portion 2 and the waist portion 3 integrated via hinged joints therebetween. The head portion 1 consists of two parts of the same or dissimilar shapes. Depending upon the sites to which these parts are applied, they assume different shapes. For instance, a racket-shaped or rectangular part is used for posterior surgical operation on fracture of vertebral body, an elliptic part is used for anterior surgical operation on fracture of vertebral body, and a semicircular part is used for surgical operation on fracture of tibial plateau, etc. The neck portion 2 consists of two semicircular tubes, and the waist portion 3 is of a tubular shape. The pull rod 7 passes through the center of the front portion of the bone dilator. At the front of the pull rod 7 are disposed bar stays 9 at both sides thereof, and the bar stays 9 are connected to the pull rod 7 and the head portion 1 via connecting pins 10. There are two pairs of bar stays 9. The pair at the proximal end side functions to prop up or fold down, and the pair at the distal end side functions, in addition to propping up or folding down, to keep the upper and lower parts of the head portion 1 parallel or at a predetermined angle. When the pull rod 7 is pulled towards the proximal end side, the bar stays 9 prop up the head portion 1 of the bone dilator just like opening an umbrella. The more the pull rod 7 is pulled back, the wider the head portion 1 of the bone dilator is expanded. Conversely, when the pull rod 7 is pushed towards the distal end side, the bar stays 9 fold down the head portion 1 of the bone dilator just like closing an umbrella. The more the pull rod 7 is pushed forwards, the closer the head portion 1 of the bone dilator is folded. When the head portion 1 is completely folded, the pull rod 7 and the bar stays 9 at both sides thereof are entirely or partially retracted into the grooves inside the head portion 1 and the neck portion 2.

2. The rear portion of the bone dilator consists of the connecting tube body 4, the handle 5 and the rotary hilt 6. The connecting tube body 4 is a hollow and thin circular tube connected respectively to the waist portion 3 via screw threads and to the handle 5 via the pin 12. The pull rod 7 passes through the center of the connecting tube body 4. At the center of the rotary hilt 6 is disposed the tension bolt 8, which is connected to the pull rod 7. When the rotary hilt 6 rotates clockwise, the pull rod 7 moves towards the proximal end side; when the rotary hilt 6 rotates counterclockwise, the pull rod 7 moves towards the distal end side. The hilt support 14 is sandwiched between the rotary hilt 6 and the handle 5, and the three are connected to one another via the fixing member 15 and the fastening screw 13. The gauge 17 is disposed at the rear of the handle 5, and the pointer 16 at the middle is connected to the pull rod 7 or the tension bolt 8. Measurement of the expansion in the head portion 1 of the bone dilator can be read in millimeter from the position of the pointer 16 on the gauge 17.

Indications for the Bone Dilator

The bone dilator is mainly suitable for treating osteoporotic compression fracture of vertebral body, and also for treating fractures of cancellous bones at other sites, such as fracture of tibial plateau, fracture of surgical neck of humerus, fracture of distal end of radius or calcaneal fracture, as well as certain traumatic or pathologic compression fracture of vertebral body, etc.

Methods for Surgical Operation:

The example of the posterior surgery for the treatment of osteoporotic compression fracture of vertebral body is used here for illustration purpose. The bone dilator for reducing the compression vertebral body is referred here as a vertebral body bone dilator. The head portion 1 of the vertebral body bone dilator is characterized in consisting of the upper and lower parts with identical shape, wherein the distal half or entire of the head portion 1 has a left-to-right diameter almost twice as large as the diameter of its rear portion, while the top-to-bottom diameter of the head portion 1 is relatively narrow and equal to the diameter of the rear portion. The head portion 1 thus assumes a racket or rectangular shape. The particular shape of the head portion 1 is set according to the height-to-width ratio of the T10 to L5 vertebral pedicles measured 2:1 on average for foreign and Chinese people. The racket-shaped or rectangular head portion 1 of the vertebral body bone dilator is longitudinally placed in the vertebral pedicle. The vertebral body bone dilator is rotated around 90 degrees after reaching the rear ½ of the vertebral body. The head portion 1 of the vertebral body bone dilator is transversely and completely placed into the vertebral body and propped up wherein, so as to increase the contact area with the upper and lower end plates upon expansion, to reduce the pressure, and to prevent cutting on the sclerotin of the vertebral body.

There are two approaches for the surgical operation:

1. Approach via Vertebral Pedicle

This approach is suitable for application to fractures of T10 to L5 vertebral bodies. The patient, who has lain prone on the operation table, is located in the level of the compressed vertebra under the fluoroscopy of a C-arm machine. The C-arm machine is then adjusted until no "double layer echo" is shown with the compressed vertebral body, that is to say, till the end plate of the vertebral body is completely parallel to the X-ray so that the end plate is imaged as a one line image. At the same time, the shapes of the vertebral pedicles at the two sides should be symmetric to one another and the distances between the spinous process to each pedicle should be equal. Now, the vertebral pedicles are shown most clearly in the anteroposterior view. After performing conventional antisepsis, surgical draping and conducting local anesthesia (or general anesthesia) on the patient, the operator should position the tip of the puncture needle at 9 o'clock of the outer edge of the left vertebral pedicle image, and at 3 o'clock of the outer edge of the right vertebral pedicle image. The C-arm machine is adjusted to be oriented in the lateral view, and the puncture needle with a core is inserted. When the tip of the needle reaches ½ of the vertebral pedicle, the tip of the needle should be located at the midline of the "eye-like" vertebral pedicle image in the anteroposterior view. If the tip of the needle is located beyond the midline and is at the inner edge of the vertebral pedicle, continued needle intrusion would run the risk of entering into the spinal canal; on the contrary, if the tip of the needle deviates too much to the outer side, the needle is likely to pass outside the vertebral body. Therefore, needle deviation in either case should be adjusted. When the tip of the needle is shown to reach the rear wall of the vertebral body in the lateral view, the tip of the needle should be shown at the inner side edge of the vertebral pedicle image in the anteroposterior view. The inner core of the puncture needle is then taken out, and a guide pin is placed in. The puncture needle cannula is pulled out, and a dilation cannula and an operation cannula are sequentially placed in along the guide pin, so that the front end of the operation cannula is located 2 mm at the front of the rear edge cortex of the vertebral body. A fine drill is slowly bored in via the operation cannula by the force of fingers. When the lateral view shows the tip of the drill reaches ½ of the vertebral body, it should be located at ½ of the line connecting the vertebral pedicle image and the spinous process in the anteroposterior view; and when in the lateral view shows the tip of the drill reaches the front edge of the vertebral body, it should be in the vicinity of the edge of the spinous process in the anteroposterior view. The fine drill is withdrawn by being rotated in the same direction as during boring-in to carry the bone chips out altogether. The dilation cannula and the operation cannula are replaced with ones having elliptic sections. A solid mould of the same size and shape as the vertebral body bone dilator is inserted into the vertebral body to form a passage, and then taken out. The vertebral body bone dilator is rotated around 90 degrees after longitudinally placed in the vertebral pedicle up to the rear half of the vertebral body along the elliptic operation cannula. By now, the wider section of the head portion 1 of the vertebral body bone dilator should face towards the upper and lower end plates. The head portion 1 is placed completely in the vertebral body beneath the lower edge of the upper end plate. The ideal location thereof is the front ¾ of the compressed vertebral body in the lateral view. By this time the head portion 1 and the neck portion 2 of the vertebral body bone dilator are all located inside the vertebral body. The rotary hilt 6 of the vertebral body bone dilator is rotated clockwise to gradually expand the vertebral body bone dilator. The expansion height of the vertebral body bone dilator can be read out from the position of the pointer 16 on the gauge 17. Meanwhile the C-arm machine monitors the circumstances of expansion of the vertebral body bone dilator. Rotation should be stopped when the upper and lower end plates of the compressed vertebral body are approximately parallel or parallel to each other. Now, bone cement PMMA (polymethylmethacrylate), or injectable bone substitute, is mixed till it is in a dough state, infused into a bone cement injection tube for standby use. The rotary hilt 6 of the vertebral body bone dilator is rotated counterclockwise to gradually fold down the vertebral body bone dilator till it is completely folded down. At this time the pointer 16 is located at the starting point of the gauge 17, and the vertebral body bone dilator is taken out after being rotated 90 degrees. By this time a cavity is formed inside the vertebral body, and the prepared PMMA is injected into the cavity in the vertebral body by means of the bone cement injection tube. This surgical bone cement injection tube has an outer diameter of 4.5 mm and an inner diameter of 3.9 mm, which is obviously larger than the bone cement injection tube with an outer diameter of 3.4 mm and an inner diameter of 2.8 mm in the cases of PV and BK. As a consequence, the timing for injecting the bone cement is significantly postponed. It is possible to inject the bone cement during its dough state, rather than during the drawing state in the cases of PV and BK. It is thus possible to markedly reduce leakage of the bone cement out of the vertebral body. If the bone cement flows out of the vertebral body during injection, the injection process would be immediately stopped. The same operation is carried out simultaneously via the vertebral pedicle at the opposite side. The patient should lie in bed for at least one hour after the operation to facilitate solidification of the bone cement.

2. Approach Outside of Vertebral Pedicle

This approach is suitable for application to fractures of T5 to T12 vertebral bodies. Since the vertebral pedicle of the thoracic vertebra has a very small gradient towards the inner side, puncture in the approach via the vertebral pedicle might break the cortex at the side of the vertebral body due to potential deviation of the inserted vertebral body bone dilator to the outer side; moreover, since the vertebral pedicle of the upper thoracic vertebra is too thin, it tends to be broken up by the dilation during operation. Through the approach via outside of the vertebral pedicle with the puncture needle entering the vertebral body from between the vertebral pedicle and the rib, it is possible for the puncture needle to have a sufficient gradient towards the inner side, so that the vertebral body bone dilator can be placed in an ideal location. Methods for the expansion of the vertebral body bone dilator and the placement of the bone cement are the same as the approach via the vertebral pedicle.

The invention claimed is:

1. A bone dilator, comprising:
  a head portion,
  a neck portion,
  a connecting tube,
  a handle and
  a rotary hilt,
  wherein the head portion and the neck portion are integrated as a whole via hinged joint therebetween;
  the head portion, the neck portion, the connecting tube and the handle are hollow bodies, through which a pull rod penetrates;
  the rotary hilt is connected to a tension bolt, which is connected to one end of the pull rod; another end of the pull rod is provided with bar stays at both sides thereof, and the two ends of the bar stays are movably connected to the pull rod and the head portion, respectively, via pins;
  a distal end of the connecting tube is movably connected to a proximal end of the neck portion, and a proximal end of the connecting tube is fixedly connected to a distal end of the handle;

a distal end of a hilt support is disposed at a proximal end side of the handle, and the rotary hilt is movably connected to a proximal end side of the hilt support, wherein when the rotary hilt is rotated clockwise and the pull rod is pulled backwards, an upper part of the head portion and a lower part of the head portion keep at a predetermined angle other than parallel during expanding, and wherein when the rotary hilt is rotated counterclockwise and the pull rod is pushed forwards, the upper and lower parts of the head portion fold; and wherein the bar stays include a proximal pair of bar stays and a distal pair of bar stays, each of the bar stays having a first end and a second end, the first ends being movably connected to the pull rod, the second ends of the distal pair of bar stays movably connected to the inside of the head portion, and the second ends of the proximal pair of bar stays being movably connected to both the distal end of the neck portion and the proximal end of the head portion via connecting pins.

2. The bone dilator according to claim 1, characterized in that the head portion consists of two parts disposed to face each other, and the neck portion assumes a shape of two semicircular tubes.

3. The bone dilator according to claim 2, characterized in that the head portion can be racket-shaped, rectangular, elliptic, circular or semicircular in accordance with different locations to which it will be applied.

4. The bone dilator according to claim 1, characterized in that a groove is formed inside the head portion and the neck portion, so that, when the head portion and the neck portion completely fold down together, the distal ends of the pull rod and the bar stays are only partially retracted in the groove inside the head portion and the neck portion.

5. The bone dilator according to claim 1, characterized in that the connecting tube is a hollow and thin circular tube, a distal end thereof being movably connected to the neck portion via a hinge, and a proximal end thereof being provided with a pin and secured to a distal end of the handle via the pin.

6. The bone dilator according to claim 1, characterized in that the connecting tube consists of a connecting tube body and a waist portion, wherein a proximal end of the connecting tube body is fixedly connected to a distal end of the handle, a distal end of the connecting tube body is fixedly connected to a proximal end of the waist portion, and a distal end of the waist portion is connected to a proximal end of the neck portion via hinged joint.

7. The bone dilator according to claim 6, characterized in that both the connecting tube body and the waist portion are hollow and thin circular tubes, a distal end of the connecting tube body is provided with screw threads, by which the connecting tube body is connected to the waist portion.

8. The bone dilator according to claim 7, characterized in that an outer diameter of the connecting tube body is less than or equal to outer diameters of the waist portion and the completely joined-together neck portion.

9. The bone dilator according to claim 1, characterized in that a pair of corresponding longitudinally-opened grooves are disposed respectively at a proximal end side of the handle and a distal end side of the hilt support, a pointer passes through the longitudinally-opened grooves of the handle and the hilt support to be fixed with the tension bolt or the pull rod, when the rotary hilt rotates clockwise or counterclockwise, the pointer may move towards the proximal end side or the distal end side, the pointer projects out of the longitudinally-opened grooves, and a gauge is provided at the edge of the opened grooves.

10. The bone dilator according to claim 1, characterized in that an annular groove is disposed on the proximal end side of the hilt support, a distal end of the rotary hilt is locked to the proximal end side of the hilt support, at least one fixing member is disposed on a sidewall of the rotary hilt, and the head portion of the fixing member is retracted in the annular groove on the peripheral surface of the hilt support, so that the rotary hilt rotates at its original location.

* * * * *